United States Patent [19]

McVay

[11] Patent Number: 4,957,492

[45] Date of Patent: Sep. 18, 1990

[54] APPARATUS FOR COLLECTING AND HANDLING TISSUE DURING UTERINE EVACUATION PROCEDURE

[75] Inventor: W. Patrick McVay, Doylestown, Pa.

[73] Assignee: Cabot Medical Corporation, Langhorne, Pa.

[21] Appl. No.: 280,946

[22] Filed: Dec. 7, 1988

[51] Int. Cl.⁵ ............................................. A61M 1/00
[52] U.S. Cl. ................................... 604/319; 604/405; 128/760
[58] Field of Search ......................... 604/317, 319–321, 604/405, 406; 128/760, 304; 55/385 C, 385 D, 159, 385.3, 385.4; 433/92; 210/460

[56] References Cited

U.S. PATENT DOCUMENTS 3,542,031 11/1970 Taylor .................................. 128/304
3,929,133 12/1975 Ragab .................................. 604/319

FOREIGN PATENT DOCUMENTS 855147 5/1940 France ................................ 604/405

Primary Examiner—J. L. Kruter
Attorney, Agent, or Firm—Shoemaker and Mattare, Ltd.

[57] ABSTRACT

A method and apparatus for the collection and handling of pathological tissue specimens during evacuative medical procedures, wherein a source of vacuum is used to draw material from a body cavity and into a collection bottle (22). In accordance with the invention, a tissue trap (21) is placed in advance of the collection bottle for filtering out and collecting tissue specimens prior to entry of the evacuated material into the collection bottle. At the end of an operative procedure, the tissue trap is removed from the system and used as a container for handling and transporting the tissue specimens, thereby avoiding the necessity of direct contact with the specimens by medical workers during the collection and transport thereof. In a preferred form of the invention, the collection bottle is disposable and includes a pour spout for emptying the contents prior to disposal of the bottle.

4 Claims, 4 Drawing Sheets

FIG. 4.
FIG. 5.
FIG. 6.
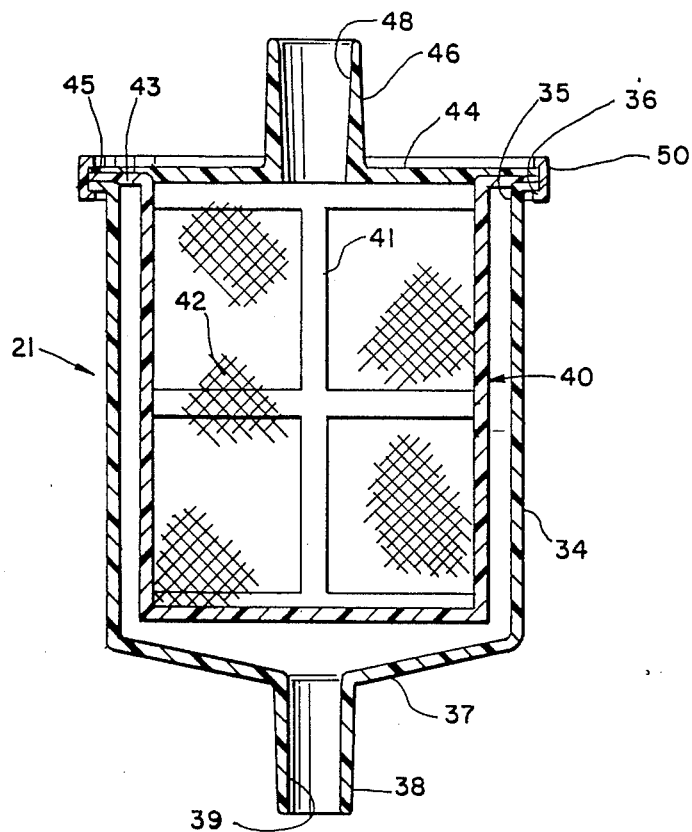
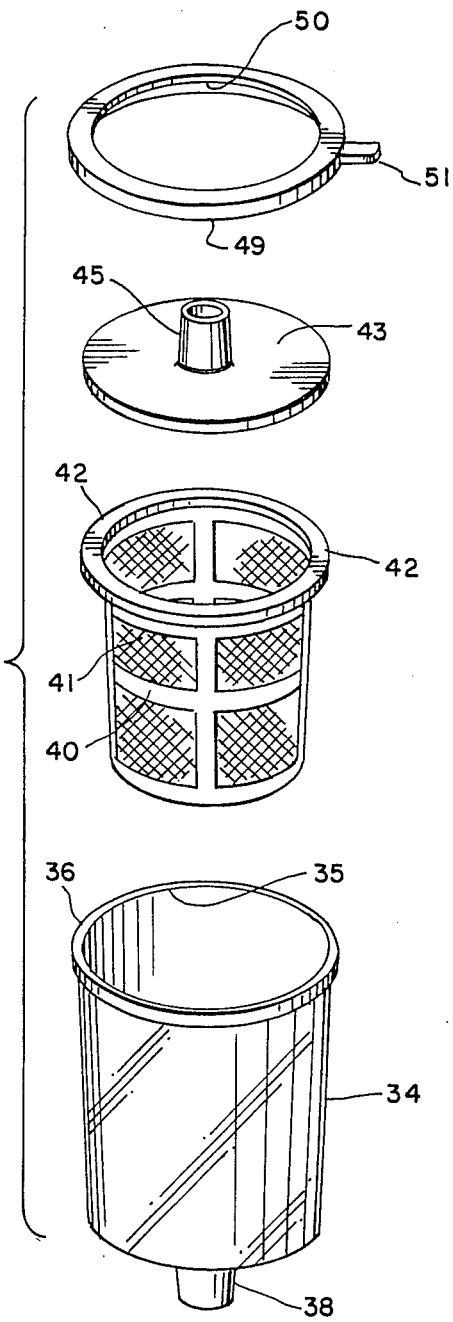
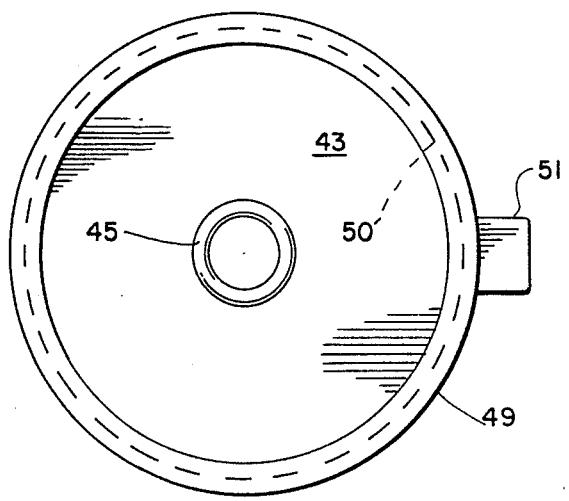

APPARATUS FOR COLLECTING AND HANDLING TISSUE DURING UTERINE EVACUATION PROCEDURE

FIELD OF THE INVENTION

This invention relates generally to medical apparatus, and more particularly, to a method and apparatus for collecting and handling tissue during uterine evacuation procedures.

PRIOR ART:

Pregnancies are sometimes terminated in the human female for a variety of reasons. Most termination procedures are performed within the first trimester of pregnancy, or within the range of six to twelve weeks from the date of conception. Such termination procedures typically involve the application of a vacuum to evacuate the products of conception from the uterus.

Conventional apparatus and methods for evacuation of the uterus involve a source of vacuum connected through a bottle with a cannula which is inserted into the uterus to draw tissue and liquid from the uterus. A gauze sack is held within the bottle for collecting tissue evacuated during the procedure, while the liquid is collected in the bottle. One prior art design uses a disposable plastic lid or cap that screws onto a reusable glass bottle, and another prior art design uses a metal lid that fits within a plastic bottle that contains a disposable plastic bag. Both of these designs require the user to reach within the bottle to remove the gauze sack that traps the evacuated tissue. The user must then dispose of the collected liquid and wash and dry either the glass bottle or the metal top to prepare for another procedure. While the disposable top solves the problem of cleaning the top, medical personnel still have to reach within the bottle to disassemble the wet and dripping sack from the top and transfer it to another sealed container for transport to a pathology lab for examination.

Other prior art designs for various evacuation procedures are disclosed in U.S. Pat. Nos. 3,773,211, 3,814,098, 3,848,628, 3,929,133, 3,955,572, 3,965,902, 4,013,076, 4,346,711, 4,516,973 and 4,455,140. With the exception of Pat. No. 3,929,133, these devices use a tissue trap inside a bottle. Pat. No. 3,929,133 uses a sieve in a transparent container external of the fluid collection bottle. As product is drawn from the patient, tissue is collected on the outside of the sieve and washed with water from a second bottle, whereby the tissue may be visually examined during the evacuation procedure. The sieve and other components of the apparatus are cleaned for use in subsequent procedures.

The problem with prior art devices as exemplified above is the potential danger to medical personnel involved in handling collected tissue. Protection of health workers from diseased and contaminated tissue is a serious matter. Since the AIDS virus (HLV-III) and hepatitis B virus may contaminate collected aborted tissue, protection is particularly critical during the teardown procedure when tissue and liquids may contact and contaminate a poorly protected worker.

SUMMARY OF THE INVENTION

Accordingly, it is an object of the present invention to provide an apparatus for medical evacuation procedures in which medical personnel are protected from contact with potentially contaminated material evacuated during the procedure.

Another object of the invention is to provide an apparatus for medical evacuation procedures, in which a sealed disposable tissue trap is positioned to intercept and filter tissue specimens from liquid evacuated during the operative procedure prior to the liquid reaching a collection bottle, said trap being separable from the apparatus and usable as a container for handling and transporting the tissue specimens following the evacuation procedure, thus avoiding the necessity of direct contact with the tissue by personnel.

A more specific object of the invention is to provide an apparatus for uterine evacuation procedures, wherein a disposable tissue collection trap is positioned externally of a liquid collection bottle, thus eliminating the necessity of reaching into the bottle to retrieve collected tissue specimens.

A further object is to provide a disposable collection bottle for collecting and disposing of liquid evacuated from a body cavity during an operative procedure.

Another object of the invention is to provide a method of collecting and handling tissue during evacuative medical procedures, comprising the steps of using a source of vacuum to evacuate material from a body cavity, collecting the material in a collection bottle for subsequent disposal, filtering solid tissue specimens from the material prior to entry of the material into the collection bottle and collecting the tissue specimens in a separate tissue trap, and removing the trap and using it as a container for handling and transport of the specimens.

In carrying out the above objects, applicant has discovered a unique and simple apparatus which incorporates a disposable rigid tissue trap outside the collection bottle for separating the pathological tissue specimen from evacuated liquid. The invention is especially suitable in uterine evacuation procedures as used, for example, in first trimester termination of pregnancy. In one form of apparatus according to the invention, most of the liquid is drawn into a plastic bag inside a collection bottle. In another, preferred form of the invention, a disposable plastic collection bottle is used and the plastic bag is omitted. Once the uterine evacuation procedure is completed, the user separates the tissue trap from the top of the collection bottle at a tapered fitting, adds formalin solution to preserve tissue and simply caps the bottom and top fittings on the tissue trap. The sealed unit is then sent to the lab where the tissue trap top is separated from the trap housing by removing a seal which serves to hold these components together. Once removed, the seal cannot be replaced and the unit is thus rendered incapable of reuse. The pathologist can then remove the filter from the assembly and remove the specimen as needed. The plastic top for the bottle and the plastic bag are removed from the bottle and disposed of. The users thus do not directly contact potentially contaminated tissue or liquid in order to handle them for transfer or disposal.

In the preferred form of the invention, the disposable collection bottle eliminates the problem of disposing of a plastic bag containing blood, as in the first form of the invention, and which has vent holes in it requiring closure prior to disposal of the bag.

While the present invention is particularly useful for termination of pregnancy, it may also be used in similar operative procedures requiring removal and retention of selected products for subsequent examination. Additionally, the invention could equally as well be used in operative procedures on animal or human subjects, for corrective, diagnostic or research purposes.

BRIEF DESCRIPTION OF THE DRAWINGS

The foregoing and other objects and advantages of the invention will become apparent from the following detailed description and accompanying drawings, wherein like reference characters designate like parts throughout the several views, and wherein:

FIG. 4 is an enlarged view in side elevation of the filter trap assembly of the invention;

FIG. 5 is a top plan view of the assembly of FIG. 4;

FIG. 6 is an exploded perspective view of the components of the filter trap assembly.

DETAILED DESCRIPTION OF THE PREFERRED EMBODIMENTS

Figure 1:
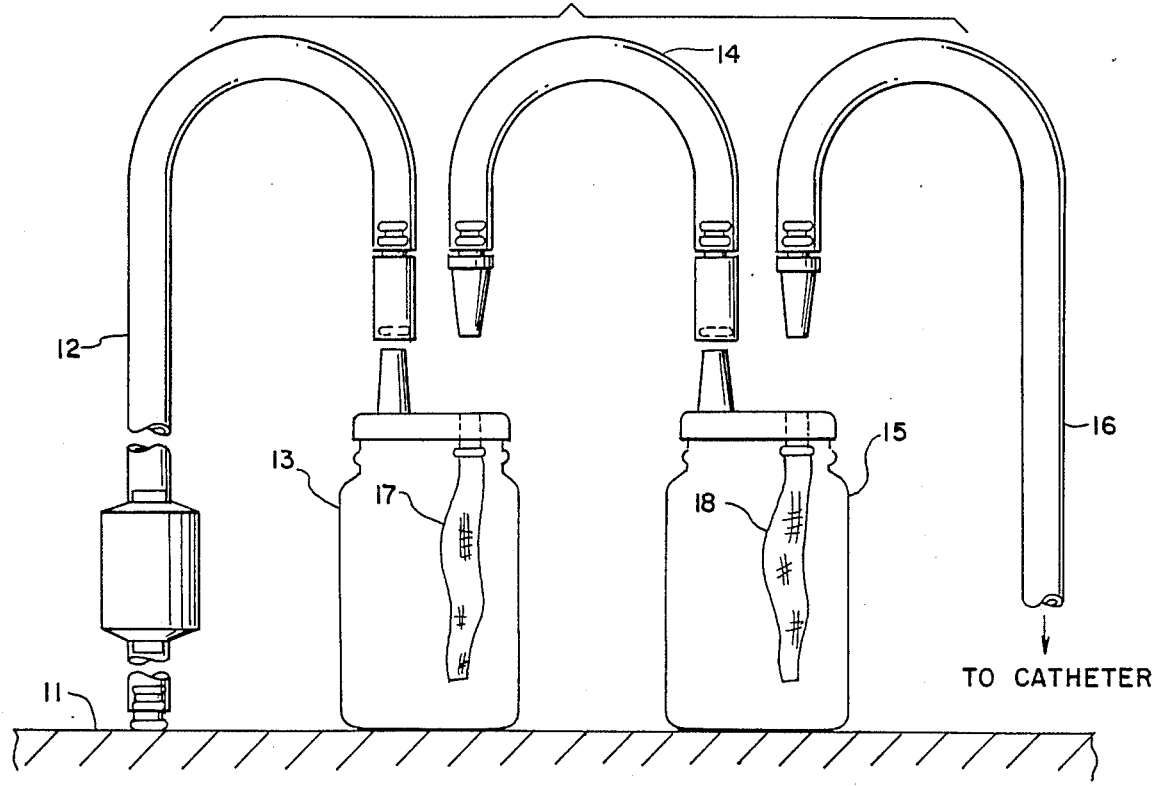
FIG. 1 is a somewhat schematic exploded view in side elevation of one prior art apparatus which uses a gauze sack inside the collection bottle to trap tissue specimens.

Referring more particularly to the drawings, a prior art apparatus is indicated generally at 10 in FIG. 1. In this apparatus, a source of vacuum 11 is connected through a hose 12 with a first collection bottle 13, which is, in turn, connected via a hose 14 with a second bottle 15. A hose 16 extends from the second bottle to a suitable device, such as a catheter, not shown, which may be inserted into a body cavity to evacuate material therefrom. Gauze sacks 17 and 18 are secured inside the collection bottles for trapping tissue specimens evacuated during the procedure, while liquid products are collected in the bottles. With this apparatus, the user is required to come into direct contact with the products of evacuation, thus endangering the user to contamination with potentially harmful diseases.

Figure 2:
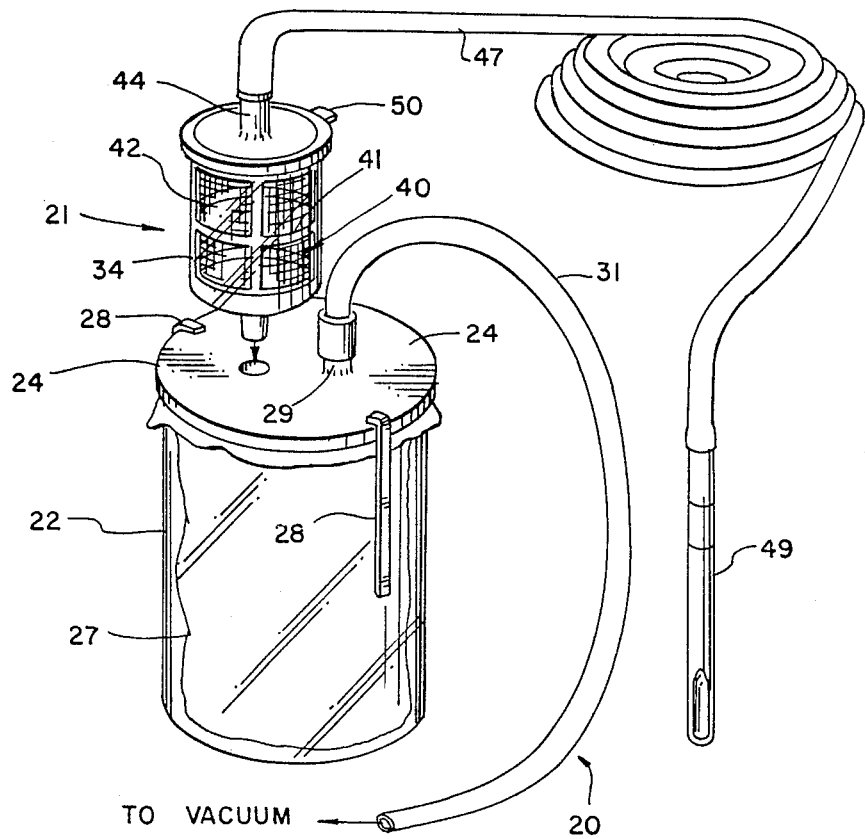
FIG. 2 is a perspective view of an apparatus in accordance with the invention.

In the apparatus of the invention, shown generally at 20 in FIG. 2, a separate disposable tissue filter trap 21 is positioned externally of the collection bottle 22, thus enabling a person using the apparatus to remove, transport and/or dispose of the products of evacuation without coming into direct contact therewith.

More specifically, in the first described form of the invention, a glass collection bottle 22 has an open top 23 to which is removably secured a lid or cover 24. The cover is preferably made of a plastic material, such as polypropylene, and includes a depending annular skirt 25 which is adapted to fit snugly inside the open top of the bottle. A radially outwardly directed peripheral flange 26 is adapted to overlie the open end of the bottle when the cover is in place, and a disposable plastic bag 27 is suitably secured to the cover by conventional means for receipt in the bottle when the cover is in place. The cover may be releasably secured to the bottle by suitable means, such as spring clips 28 or the like.

An upstanding nipple or tapered fitting 29 is formed in the cover to one side of the center thereof, and an opening 30 extends therethrough. A length of hose 31 is attached at one end to the nipple and extends at its other end into operative connection with a source of vacuum (not shown). Thus, the interior of the bottle is placed under a vacuum.

A second, depending nipple or tapered fitting 32 is formed in the cover in spaced relation to the first fitting for supporting the tissue trap 21, and an opening 33 extends through the nipple whereby the vacuum through hose 31 and in bottle 22 is communicated to the interior of the tissue trap.

Figure 3:
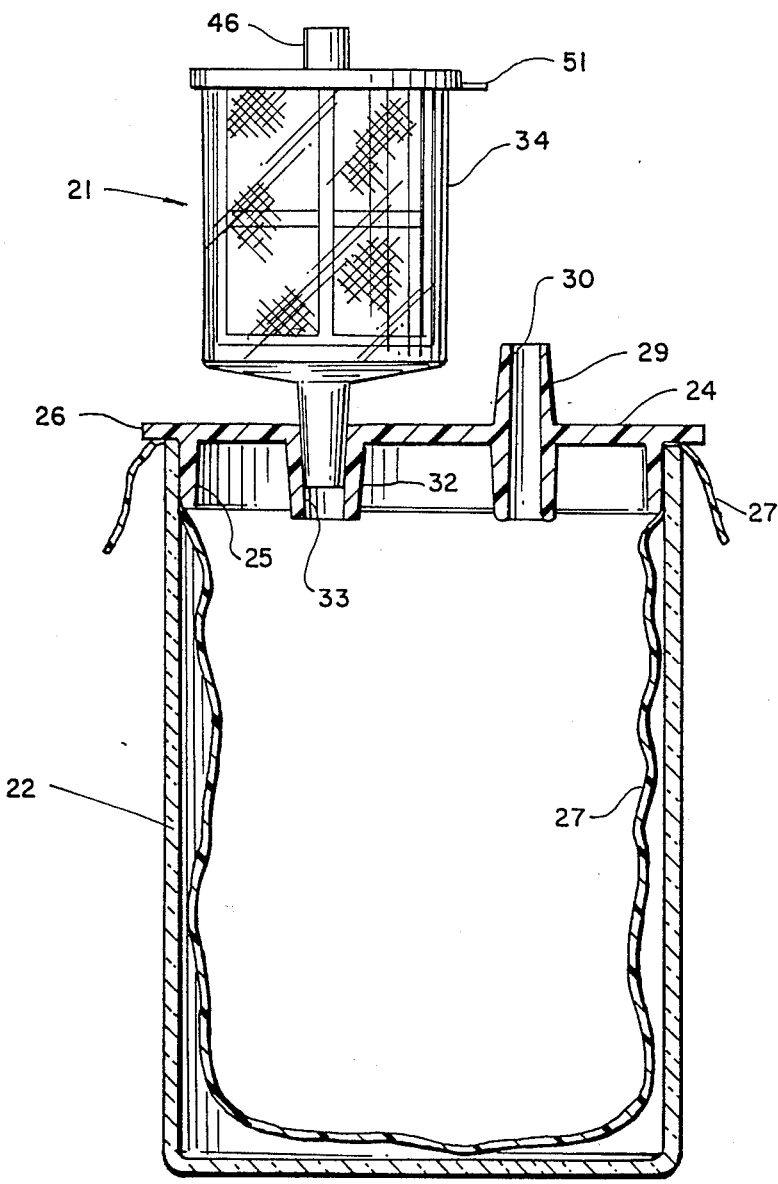
FIG. 3 is an enlarged longitudinal sectional view of the collection bottle, cap, plastic bag and filter trap of the invention.
Figure 7:
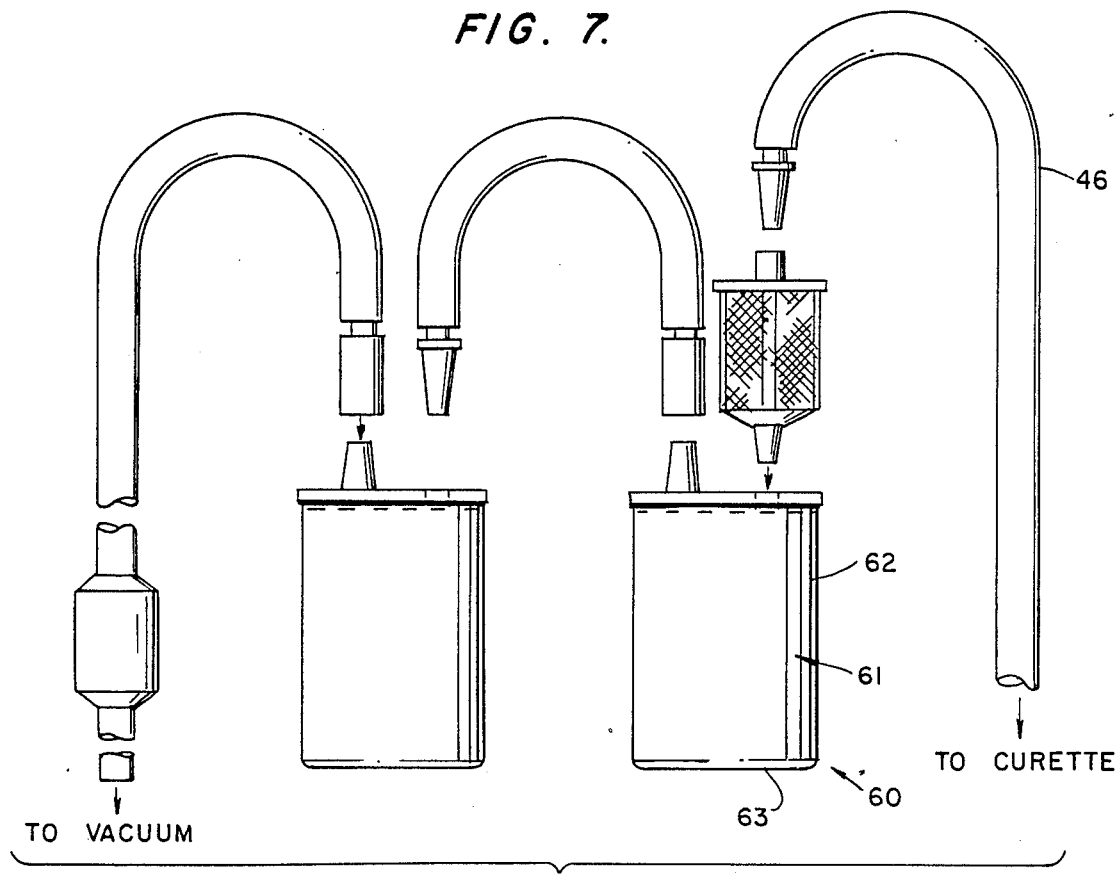
FIG. 7 is an exploded schematic view in side elevation of a preferred form of the invention, in which the plastic bag inside the collection bottle is eliminated, and a disposable plastic collection bottle is used instead.
Figure 8:
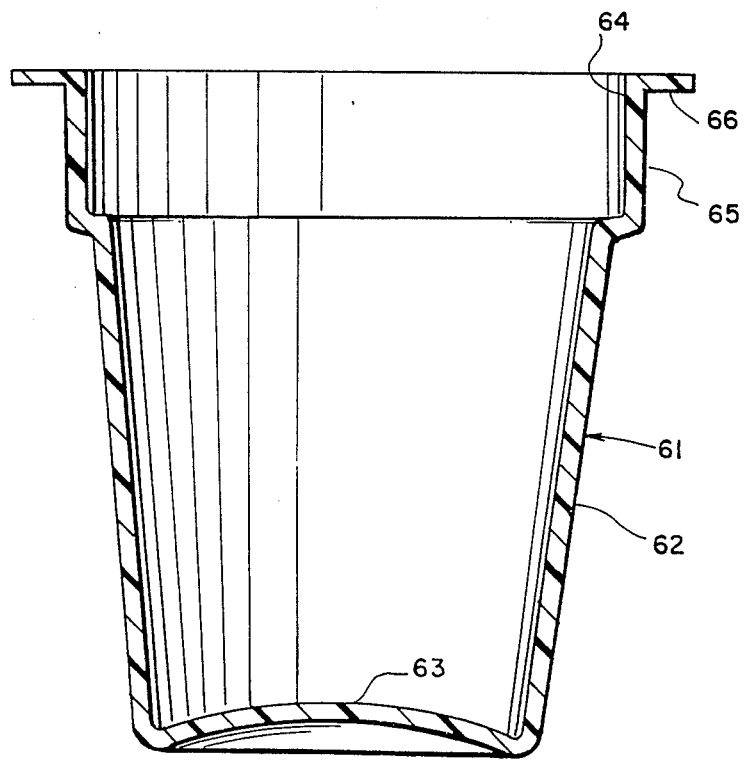
FIG. 8 is an enlarged vertical sectional view of the disposable collection bottle of FIG. 7.
Figure 9:
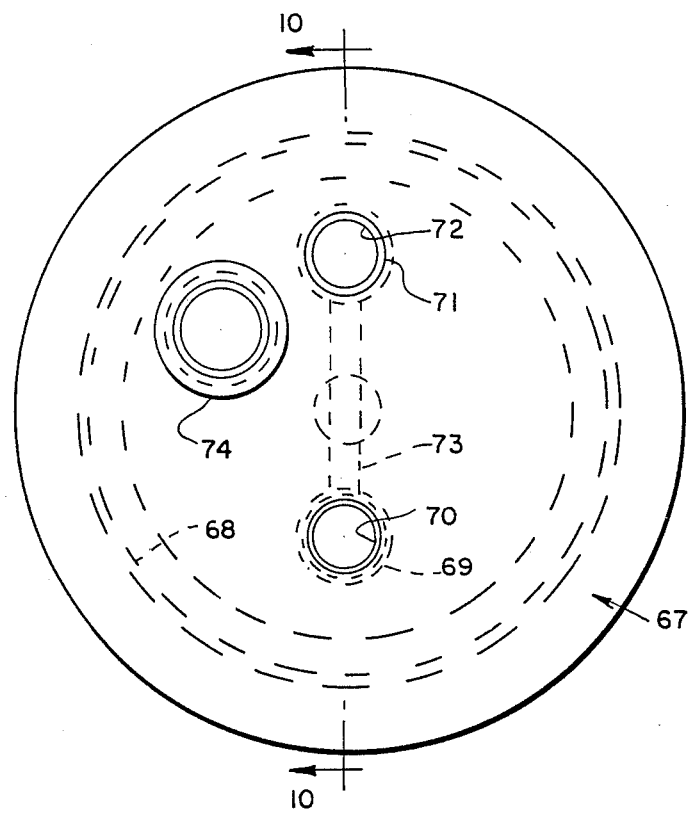
FIG. 9 is a top plan view of the top for the disposable collection bottle of FIG. 7.
Figure 10:
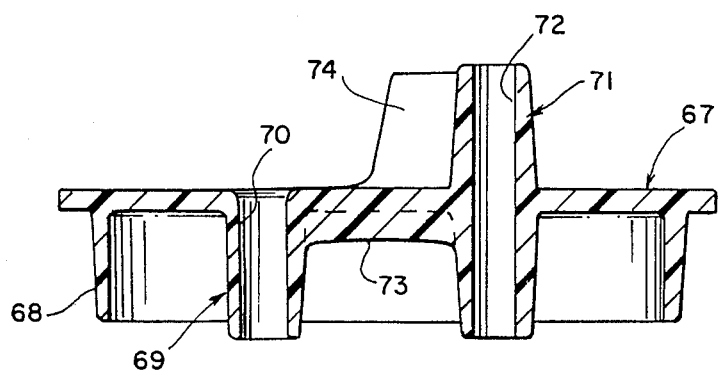
FIG. 10 is a view in section of the top, taken along line 10—10 in FIG. 9.

As seen best in FIGS. 2, 3 and 4, the tissue trap 21 comprises a housing 34 having an open end 35 with an annular, outwardly projecting flange 36 thereon, and a closed end 37. A depending nipple 38 projects downwardly from the center of the closed end, and an opening 39 extends therethrough. The nipple 38 has a taper shaped to conform to the internal taper in the fitting 32 in the cover of the bottle, whereby the housing 34 may be supported on the cover by engaging the tapered nipple 38 in the tapered fitting 32.

A filter element 39 is removably held in the housing 34 and comprises an open frame 40 with a mesh screen 41 secured thereon. The frame 40 has a radially enlarged flange 42 on an open upper end thereof, adapted to overlie the flange 36 on the housing.

The open end of the housing is closed by a disc-shaped cover or lid 43, which extends at its outer marginal edge 44 in overlying relationship with the flange 42 on the filter element frame, sandwiching the filter element flange between the cover 43 and the housing 34. An upstanding nipple 45 is formed in the center of the cover for attachment of a length of hose 46, and an opening 47 extends through the nipple, establishing communication between the interior of the filter element and the hose. As shown in FIG. 2, a vacuum assisted curette 48 is secured to the other end of the hose 46.

The cover, filter element and housing are held in sealed, assembled relationship to one another by a flexible annular band 49. As seen best in FIGS. 4, 5 and 6, the band 49 is formed with a radially inwardly facing channel 50 which closely receives the flanges of the housing, cover and filter element, and includes an outwardly protruding tab 51 whereby the tab may be grasped to peel the band from the assembly to enable the cover and thus the filter element to be removed from the housing. Once this seal has been removed, it cannot be replaced, thus rendering the trap incapable of reuse.

In use, the curette is inserted into a body cavity, such as the uterus, and the source of vacuum operated to establish a vacuum through the hose 31 and thence through the bottle 22, tissue trap 21, hose 46 and vacurette 48 to evacuate material from the cavity. Liquids and solid material are drawn through the hose 46 and tissue trap 21, where the solid materials are trapped by the filter element 39. Liquid material flows through the filter and into the disposable plastic bag 27 inside the collection bottle 22. Upon completion of an evacuation procedure, the user removes the hose 46 from the tissue trap cover 43 and separates the tissue trap from the collection bottle cover 24. A 10% Formalin phosphate solution can be added to preserve the collected tissue during transport. The top and bottom fittings 45 and 38 are then capped with suitable closures and the sealed tissue trap sent to the lab for analysis of the tissue contained therein. At the lab, the pathologist grasps the tab 51 and removes the band 49, whereupon the filter element 39 may be lifted from the housing 34. The specimen contained in the filter element can then be removed as needed. The plastic top or cover 24 for the collection bottle, and the disposable plastic bag are removed from the bottle and disposed of. The remaining components may be drained for reuse or discarded, as desired. Medical personnel handling the apparatus thus need never come into direct contact with the materials evacuated during the procedure, minimizing the risk of exposure to communicable diseases.

In the design of the tissue trap for use in uterine evacuation procedures, it is important to consider the need to trap specimens from a first trimester pregnancy. Most termination procedures are effected within a range of from six to twelve weeks from conception. The characteristics and volume of the evacuated tissue change substantially during this period. It is thus necessary that the filter media or screen is properly sized in order to trap enough tissue from a six week termination without excessive clogging and overfilling from a twelve week termination. Best results have been found with Tetko type 3-1190/66 woven nylon mesh, in a range of mesh sizes from about 1,000 up to about 1,400 microns. Openings larger than 1,400 microns lose too much specimen, and openings smaller than 1,000 microns clog and overfill the tissue trap with too much liquid. In a specific example of the invention, the filter element frame 40 may be made from modified styrene, polyamide or polypropylene, and the sealing band 49 may comprise Kraton rubber, having a wall thickness of 0.050 inches.

In the preferred form of the invention, represented generally at 60 in FIGS. 7–10, a disposable plastic collection bottle 61 is used in lieu of the glass bottle 22 and disposable plastic bag 27 of FIGS. 2–6. The bottle 61 comprises a side wall 62 having a closed bottom 63 and an open top 64. As seen best in FIG. 8, the open top is diametrically enlarged at 65 and has a radially outwardly extending flange 66 thereon.

A top 67 closes the open end of the collection bottle and has a depending annular flange 68 adapted to fit snugly inside the enlarged open end of the bottle, effecting a seal therewith. A female fitting 69 with an opening 70 therethrough is formed in the top adjacent one side thereof for receipt of the nipple 38 on the bottom end of the trap 21, and a male fitting or nipple 71 with an opening 72 therethrough is formed adjacent the other side of the top for connection to the length of tubing 31 leading to the vacuum pump. As seen best in FIG. 10, a reinforcing web 73 extends across the bottom side of the top between the two fittings. A pour spout 74 is also provided in the top for emptying the collected liquid down a sanitary drain. After the bottle has been emptied, caps (not shown) are placed on the openings and the bottle is disposed of in a suitable manner, as by incinerating, etc.

Although the invention has been described with reference to particular embodiments, it is to be understood that this embodiment is merely illustrative of the application of the principles of the invention. Numerous modifications may be made therein and other arrangements may be devised without departing from the spirit and scope of the invention.

I claim:

1. In an apparatus for collecting tissue during evacuative medical procedures, wherein the apparatus includes a source of vacuum, a liquid collection bottle, a vacuum curette sized to enter a body cavity for withdrawing material during the procedure, a first hose connected between the source of vacuum and the bottle, and a second hose connected from the bottle to the vacuum curette, the improvement comprising:

a tissue trap connected in the hose from the vacuum curette to the collection bottle, externally of the bottle, for trapping tissue as evacuated material is drawn from a body cavity and into the bottle, said tissue trap including a filter element for receiving and holding tissue therein while passing liquid material to the bottle, said liquid collection bottle having an open end closed by a lid, said lid having a first fitting for attachment of the hose leading to the source of vacuum, and a second fitting for attachment of the tissue trap, said tissue trap having a fitting for complemental engagement with the fitting in the collection bottle lid to releasably hold the tissue trap to the collection bottle, said filter element held in said housing beneath a cover and removable through the open end upon removal of the cover; and including an open frame with an annular, radially outwardly directed flange thereon disposed in overlying relationship with the flange on the tissue trap housing, said housing having a removable cover on one end, said housing further having an open end and an opposite, closed end, said cover being on said open end and said fitting being on said closed end, the open end of said tissue trap housing having a radially outwardly directed flange thereon disposed in overlying relationship with the filter element flange, thereby sandwiching the filter element flange between the housing flange and cover flange to seal and hold the filter element in place, and a releasable sealing means engaged with the housing, cover and filter element to retain them in sealed, assembled relationship to one another.

2. An apparatus as claimed in claim 1, wherein:

said releasable sealing means comprises an annular, flexible band having a radially inwardly facing channel in which said flanges are engaged, whereby the flanges are held in sealed, assembled relationship to one another.

3. An apparatus as claimed in claim 1, wherein:

said tissue trap housing cover has a fitting centrally disposed thereon for attachment thereto of the hose leading to the curette; and said filter element is supported beneath said cover so that all material evacuated from the body cavity is caused to flow into the filter element, whereupon solid tissue or material becomes trapped in the filter and liquid material flows through the filter to the collection bottle, said tissue trap defining a container for holding the solid material therewithin, whereby the tissue trap may be used for transport and/or disposal of the tissue contained therein.

4. An apparatus as claimed in claim 1, wherein: said tissue trap is disposable.

* * * * *